US012582341B2

(12) United States Patent
Ricci et al.

(10) Patent No.: US 12,582,341 B2
(45) Date of Patent: Mar. 24, 2026

(54) SYSTEM FOR DETECTING QRS COMPLEXES IN AN ELECTROCARDIOGRAMY (ECG) SIGNAL

(71) Applicant: Murata Vios, Inc., Woodbury, MN (US)

(72) Inventors: Carlos A. Ricci, Apple Valley, MN (US); Vladimir V. Kovtun, Inver Grove Heights, MN (US)

(73) Assignee: Vios Medical, Inc., Woodbury, MN (US)

( * ) Notice: Subject to any disclaimer, the term of this patent is extended or adjusted under 35 U.S.C. 154(b) by 661 days.

(21) Appl. No.: 16/880,320

(22) Filed: May 21, 2020

(65) Prior Publication Data

US 2020/0390355 A1 Dec. 17, 2020

Related U.S. Application Data

(60) Provisional application No. 62/859,974, filed on Jun. 11, 2019.

(51) Int. Cl.
*A61B 5/316* (2021.01)
*G16H 50/30* (2018.01)
*H03H 17/02* (2006.01)

(52) U.S. Cl.
CPC ............. *A61B 5/316* (2021.01); *G16H 50/30* (2018.01); *H03H 17/0248* (2013.01); *H03H 17/0266* (2013.01); *G06F 2218/10* (2023.01)

(58) Field of Classification Search
CPC ....... A61B 5/318; A61B 5/316; G06K 9/0053
See application file for complete search history.

(56) References Cited

U.S. PATENT DOCUMENTS

| | | | |
|---|---|---|---|
| 7,702,502 | B2 | 4/2010 | Ricci et al. |
| 7,706,992 | B2 | 4/2010 | Ricci et al. |
| 8,086,304 | B2 | 12/2011 | Brockway et al. |
| 9,530,425 | B2 | 12/2016 | Ricci et al. |

(Continued)

OTHER PUBLICATIONS

International Search Report and Written Opinion in International Application No. PCT/US2020/034173, Jul. 28, 2020, 15 pages.

*Primary Examiner* — Amanda L Steinberg
*Assistant Examiner* — Jessica L Mullins
(74) *Attorney, Agent, or Firm* — Keating & Bennett, LLP

(57) ABSTRACT

In one aspect, a computer-implemented method includes receiving a signal corresponding to electrical activity of a patient's heart; separating the signal into component signals; detecting fractional phase transitions for each of the component signals; generating, at each of the detected fractional phase transitions for each of the component signals, a data object containing a time value and an amplitude value; for a set of consecutive data objects associated with a first component signal of the component signals, detecting a peak amplitude; for a set of consecutive data objects associated with a second component signal of the component signals, detecting a peak amplitude; determining that the peak amplitudes satisfy a first time; calculating a consolidated peak amplitude and a consolidated peak time; and in response to determining that the consolidated peak amplitude satisfies both an amplitude criterion and a second time criterion, providing an indication of a detected heartbeat.

37 Claims, 8 Drawing Sheets

(56)     References Cited

U.S. PATENT DOCUMENTS

2008/0119748 A1* 5/2008 Palreddy ................. A61B 5/35
                                                    600/516
2011/0201951 A1* 8/2011 Zhang ................... A61B 5/352
                                                    600/509
2014/0289297 A1   9/2014 Ricci et al.

* cited by examiner

200

300

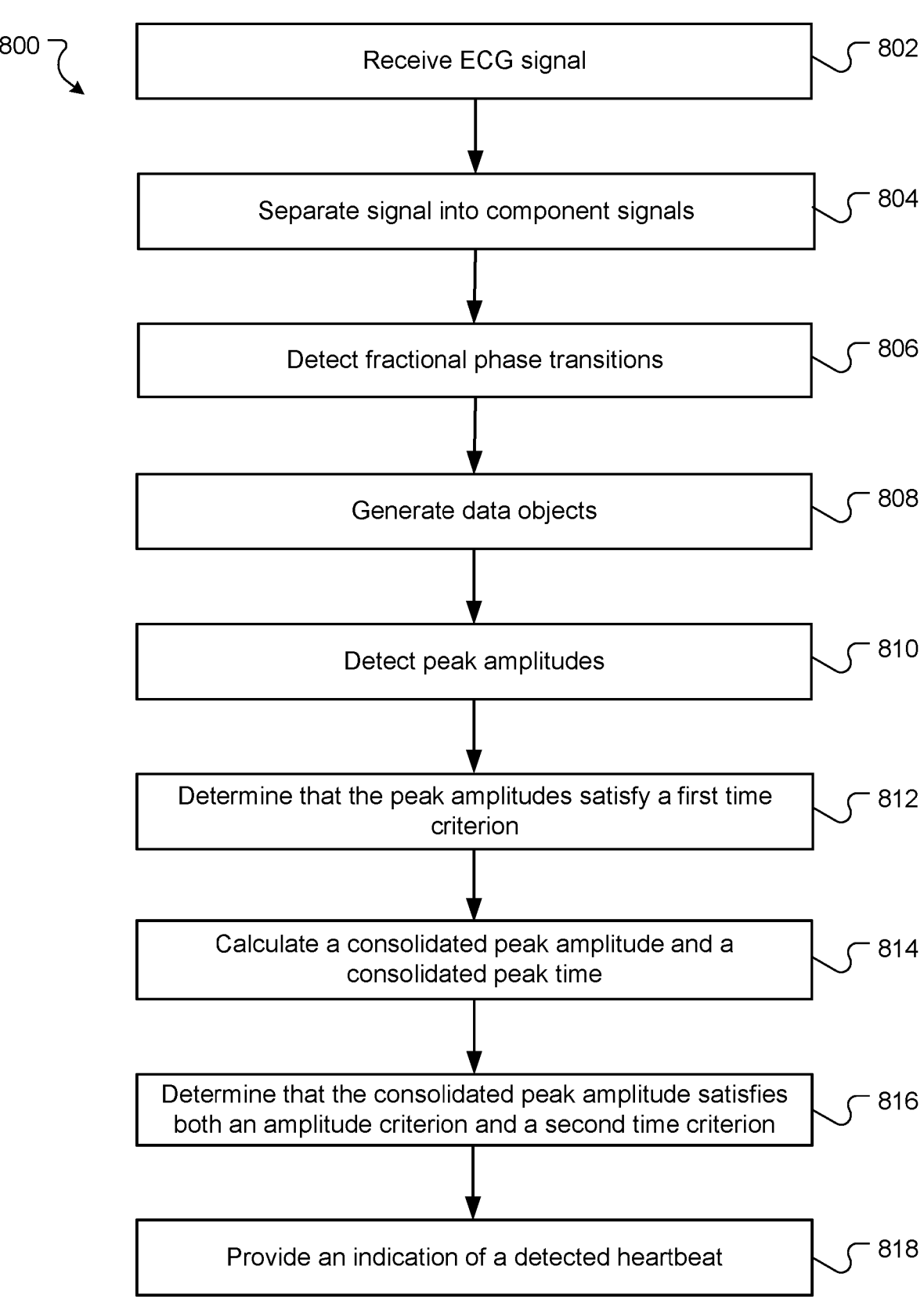

800

Receive ECG signal — 802

Separate signal into component signals — 804

Detect fractional phase transitions — 806

Generate data objects — 808

Detect peak amplitudes — 810

Determine that the peak amplitudes satisfy a first time criterion — 812

Calculate a consolidated peak amplitude and a consolidated peak time — 814

Determine that the consolidated peak amplitude satisfies both an amplitude criterion and a second time criterion — 816

Provide an indication of a detected heartbeat — 818

FIG. 8

SYSTEM FOR DETECTING QRS COMPLEXES IN AN ELECTROCARDIOGRAMY (ECG) SIGNAL

CROSS-REFERENCE TO RELATED APPLICATIONS

This application claims the benefit of U.S. Provisional Application No. 62/859,974, filed on Jun. 11, 2019. The contents of this aforementioned application being fully incorporated herein by reference.

BACKGROUND

This disclosure relates to electrocardiography signal processing.

Electrocardiography (ECG or EKG) is the process of recording the electrical activity of a patient's heart over a period of time using electrodes placed on the patient's skin. The electrodes measure the electrical changes on the skin corresponding to the electrical charges generated by the heart during each heartbeat. The heart's electrical activity is represented by an ECG signal, which includes three main components: the P wave, the QRS complex, and the T wave. The P wave represents atrial depolarization, the QRS complex represents ventricular depolarization, and the T wave represents ventricular repolarization.

These three components each have a fairly unique pattern, and changes in the structure of the heart and its surroundings (including blood composition) change the patterns of these components. As such, an ECG signal can convey a large amount of information about the structure and function of the heart. Among other things, ECG can be used to measure the rate and rhythm of heartbeats, the size and position of the heart chambers, the presence of any damage to the heart's muscle cells or conduction system, the effects of heart drugs, and the function of implanted pacemakers.

An ECG signal can include artifacts, which are distorted signals caused by secondary internal or external sources such as muscle movement or interference from an electrical device. Certain artifacts pose significant challenges to correctly identifying and diagnosing rhythm disturbances. For example, some rhythmic motions, such as shivering or tremors, can create the illusion of cardiac arrhythmia. Thus, accurately separating an ECG artifact from the true ECG signal can have a significant impact on patient outcomes.

SUMMARY

This disclosure describes systems and techniques related to ECG signal processing. The described systems and techniques can be used to detect QRS complexes within the ECG signal. This disclosure incorporates by reference the entire contents of U.S. Pat. No. 7,702,502 filed Feb. 23, 2006, titled "Apparatus for Signal Decomposition, Analysis and Reconstruction," U.S. Pat. No. 7,706,992 filed Feb. 23, 2006, titled "System and Method for Signal Decomposition, Analysis and Reconstruction," U.S. Pat. No. 8,086,304 filed Nov. 26, 2008, titled "Physiological Signal Processing to Determine a Cardiac Condition," and U.S. Pat. No. 9,530, 425 filed Mar. 17, 2014, titled "Method and Apparatus for Signal Decomposition, Analysis, Reconstruction and Tracking," which include disclosures of signal decomposition and analysis techniques that are applicable to the processing of ECG signals and that can provide for sophisticated signal analysis at relatively low computational cost. By utilizing the previously patented signal decomposition and analysis techniques, the presently described systems and techniques may enable high performance in detection of QRS complexes and high robustness to artifacts in the ECG signal (e.g., Sensitivity/Positive Predictivity>99.6% on the MIT-BIH Arrhythmia Database).

U.S. Pat. No. 7,706,992 describes systems and techniques for a quasi-periodic decomposition of the ECG signal through a set of band-limited analytic wavelets, aligned to frequency ranges that are known to be associated with important features of the cardiac signal (e.g., proceeding from high to low frequencies: Late Potentials, QRS complex, T-wave, Heart Rate frequency, T-wave Alternans, and circadian rhythm). The wavelets can be very computationally efficient, using few numerical operations, while still maintaining band separation and linear-phase response. The wavelet outputs, expressed as functions of time, form component signals exhibiting the property that their extrema and zero-crossings coincide with time points that are consistently associated with significant morphological features of the ECG signal (also referred to as "significant points"). Time marks are generated at these time points, along with various labels and attributes describing the state of the associated wavelets at those points. Taken in combination, this information provides a means to encode the significant points into objects, thus generating one stream of objects per wavelet component. Combining the objects into a time-aligned vector forms state sequences that are uniquely associated with morphologic features in the underlying signal. By observing the state sequences in state space, methods of pattern analysis and recognition can be applied, which can result in precise segmentation (detection and measurement of the various morphologic features) of the ECG.

In general, in one innovative aspect, a system includes a display apparatus, one or more data processing apparatus coupled with the sensor and the display apparatus, and a non-transitory computer readable storage medium encoded with a computer program, the program comprising instructions that when executed by the one or more data processing apparatus cause the one or more data processing apparatus to perform operations. The operations include receiving a signal corresponding to electrical activity of a patient's heart; separating the signal into component signals, wherein each of the component signals represents a frequency-limited band; detecting fractional phase transitions for each of the component signals; generating, at each of the detected fractional phase transitions for each of the component signals, a data object containing a time value and an amplitude value; for a set of consecutive data objects associated with a first component signal of the component signals, detecting a peak amplitude based on the amplitude value of each data object of the set of consecutive data objects; for a set of consecutive data objects associated with a second component signal of the component signals, detecting a peak amplitude based on the amplitude value of each data object of the set of consecutive data objects; determining that the peak amplitudes satisfy a first time criterion based on the time values of the data objects corresponding to the peak amplitudes; calculating a consolidated peak amplitude and a consolidated peak time based on the peak amplitudes and the time values of the data objects corresponding to the peak amplitudes; determining that the consolidated peak amplitude satisfies both an amplitude criterion and a second time criterion; and in response to determining that the consolidated peak amplitude satisfies both the amplitude criterion and the second time criterion, providing an indication of a detected heartbeat.

In another aspect, an apparatus includes a non-transitory computer readable storage medium encoded with a computer program. The program includes instructions that when executed by the one or more data processing apparatus cause the one or more data processing apparatus to perform operations. The operations include receiving a signal corresponding to electrical activity of a patient's heart; separating the signal into component signals, wherein each of the component signals represents a frequency-limited band; detecting fractional phase transitions for each of the component signals; generating, at each of the detected fractional phase transitions for each of the component signals, a data object containing a time value and an amplitude value; for a set of consecutive data objects associated with a first component signal of the component signals, detecting a peak amplitude based on the amplitude value of each data object of the set of consecutive data objects; for a set of consecutive data objects associated with a second component signal of the component signals, detecting a peak amplitude based on the amplitude value of each data object of the set of consecutive data objects; determining that the peak amplitudes satisfy a first time criterion based on the time values of the data objects corresponding to the peak amplitudes; calculating a consolidated peak amplitude and a consolidated peak time based on the peak amplitudes and the time values of the data objects corresponding to the peak amplitudes; determining that the consolidated peak amplitude satisfies both an amplitude criterion and a second time criterion; and in response to determining that the consolidated peak amplitude satisfies both the amplitude criterion and the second time criterion, providing an indication of a detected heartbeat.

In another aspect, a computer-implemented method includes receiving a signal corresponding to electrical activity of a patient's heart; separating the signal into component signals, wherein each of the component signals represents a frequency-limited band; detecting fractional phase transitions for each of the component signals; generating, at each of the detected fractional phase transitions for each of the component signals, a data object containing a time value and an amplitude value; for a set of consecutive data objects associated with a first component signal of the component signals, detecting a peak amplitude based on the amplitude value of each data object of the set of consecutive data objects; for a set of consecutive data objects associated with a second component signal of the component signals, detecting a peak amplitude based on the amplitude value of each data object of the set of consecutive data objects; determining that the peak amplitudes satisfy a first time criterion based on the time values of the data objects corresponding to the peak amplitudes; calculating a consolidated peak amplitude and a consolidated peak time based on the peak amplitudes and the time values of the data objects corresponding to the peak amplitudes; determining that the consolidated peak amplitude satisfies both an amplitude criterion and a second time criterion; and in response to determining that the consolidated peak amplitude satisfies both the amplitude criterion and the second time criterion, providing an indication of a detected heartbeat.

Various other functions and benefits of such systems and methods will be apparent from the foregoing detailed description and claims.

DESCRIPTION OF DRAWINGS

FIG. 8 is a flowchart showing examples of operations performed by an ECG signal processing system.

Like reference numbers and designations in the various drawings indicate like elements.

DETAILED DESCRIPTION

Figure 1:
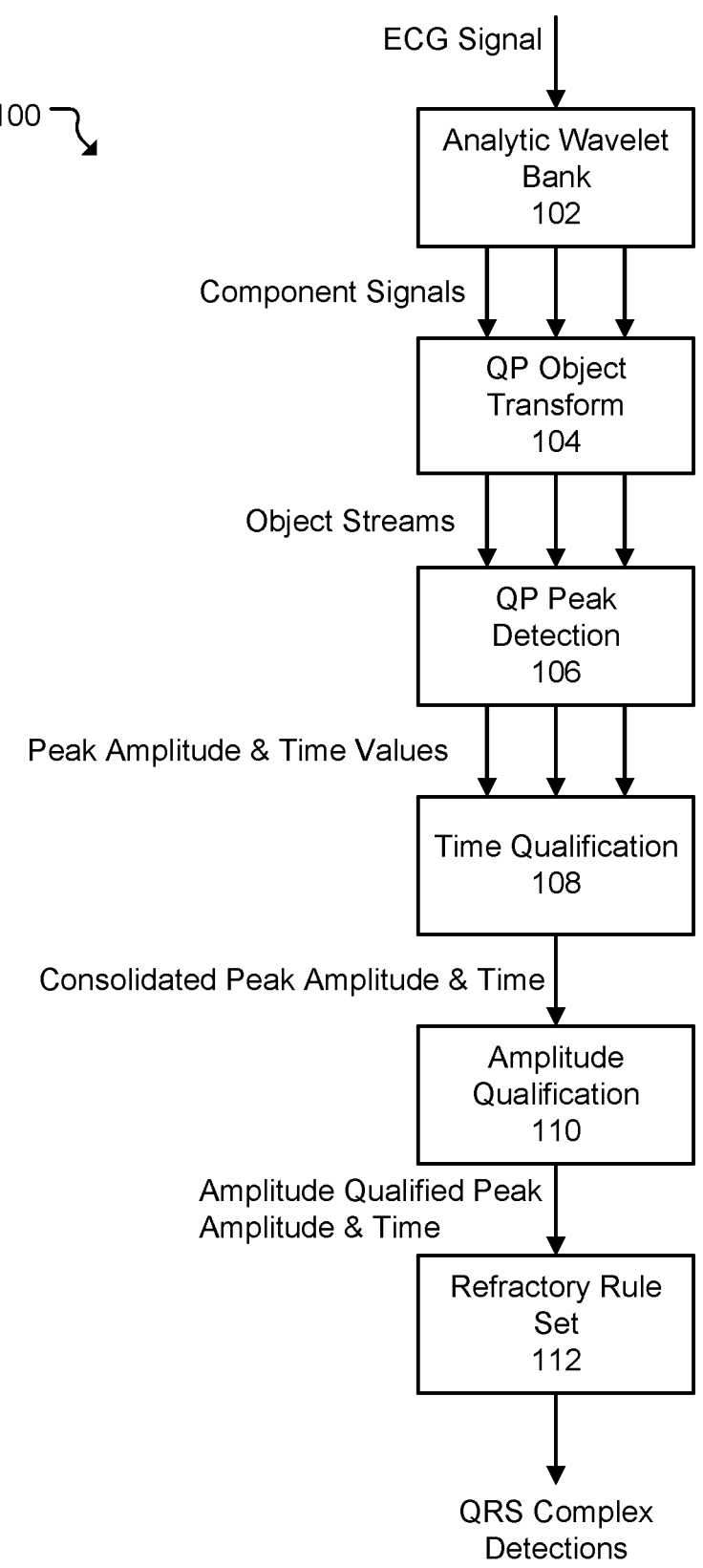
FIG. 1 is a block diagram showing an example of an ECG signal processing system that detects QRS complexes.

FIG. 1 is a block diagram showing an example of an ECG signal processing system 100 that detects QRS complexes within the ECG signal. The system 100 includes electronic components, e.g., hardware and/or software that facilitate ECG signal processing. In some implementations, portions of the system 100 are included in a patient monitoring device that can continuously collect physiological vital signs data, such as ECG waveforms, heart rate, respiratory rate, oxygen saturation, blood pressure, temperature, and pulse rate. Examples of patient monitoring devices include chest sensors, such as those described in U.S. Publication No. 2015/0302539, filed Oct. 22, 2015, titled "Patient Care and Health Information Management Systems and Methods" and U.S. Publication No. 2016/0228060, filed Feb. 9, 2016, titled "Patient Worn Sensor Assembly," and other sensor assemblies that connect with peripheral devices, such as the sensor assembly described in U.S Publication No. 2018/0213859, filed Jan. 25, 2018, titled "Sensor Connection Assembly for Integration with Garment," the disclosures of which are hereby incorporated by reference in their entirety. In some implementations, portions of the system 100 are included in a monitoring station that analyzes and displays physiological vital signs data using signals received from one or more peripheral devices, such as a chest sensor, a fingertip probe, an earlobe probe, or a non-invasive blood pressure (NIBP) cuff. Examples of monitoring stations include a bedside monitor and a central server station which are also described in U.S. Publication No. 2015/0302539.

The system 100 includes an analytic wavelet bank 102, a quarter-phase (QP) object transform unit 104, and a QP peak detection unit 106, a time qualification unit 108, an amplitude qualification unit 110, and a refractory rule set 112. The ECG signal that is provided to the system 100 may be a filtered ECG signal. The ECG signal may be filtered using conventional techniques to suppress baseline wander and low-frequency artifacts below 0.5 Hz and high-frequency noise and artifacts above 55 Hz. The filtered ECG signal is first processed with the analytic wavelet bank 102 to decompose (separate) the signal into a set of time-frequency scales associated with key morphological components of QRS complexes. This results in component signals that are provided to the QP object transform unit 104, which applies a QP transform (as described in U.S. Pat. No. 7,706,992) to detect the extrema and zero-crossings of the component signals. These points are associated with points along the ECG signal having significant morphological features. The QP object transform unit 104 additionally extracts key information embedded within the ECG signal, in this case, information associated with QRS complexes, and embeds this information into QP objects. This process results in streams of QP objects that are provided to the QP peak detection unit 106, which applies rules for detection of patterns associated with QRS complex peaks, followed by the time qualification unit 108, the amplitude qualification unit 110, and refractory rule set 112, which apply rules for qualification of those peaks as QRS complex detections. The QRS complex detections provided by system 100 can be used to identify heart beats and calculate heart rate statistics.

The analytic wavelet bank 102 can be implemented as a Parallel-Form Kovtun-Ricci Wavelet Transform using, for example, three analytic component bands (see U.S. Pat. No. 7,706,992). As described in U.S. Pat. No. 7,706,992, the wavelets are composed of a cascade of scaled-derivative kernels and scaled-integral kernels. The scaled-derivative kernel has a z-domain transfer function:

$$H_{dp}(z)=[0.5(1-z^{-k_p})]^{N_{dp}}$$

having scale parameter $k_p$ and order parameter $N_{dp}$ for band p. Observed in a broadband sense, the scaled-derivative kernel acts as a comb filter, i.e., a filter having repeating lobes over frequency. Band-limiting its response to isolate its first lobe obtains a pure bandpass response. The scaled-integral kernel described in U.S. Pat. No. 7,706,992 can accomplish a lowpass operation efficiently by performing a moving-average lowpass through the transfer function $$H_{ip}(z) = \left[ \frac{1 - z^{-w_p}}{w_p(1 - z^{-1})} \right]^{N_{ip}}$$

having scale parameter $w_p$ and order parameter $N_{ip}$ for band p.

As described in U.S. Pat. No. 7,706,992, scale parameter $k_p$ of the transform wavelet controls the peak of the fundamental bandpass lobe, while scale parameter $w_p$ determines the frequency of the first null of the lowpass. Choosing the nominal value of $w_p \approx 2\ k_p/3$ places that first null approximately at the peak of the second bandpass lobe of $H_{dp}(z)$, i.e., the first repeat of the comb, thus effectively isolating the fundamental bandpass response. Integral-order parameter $N_{ip}$ controls the degree of stop-band attenuation for the lowpass operation; a value of $N_{ip}=4$ may provide highly effective performance at low computational load. Derivative-order parameter $N_{dp}$ controls the bandwidth of the bandpass function. For a filter bank, it controls the amount of overlap between the band responses. For the QRS bank, the values of $N_{dp}$ are chosen so that the sum of the band responses is approximately flat over the QRS power band, so that the total power of the QRS complex is represented in a relatively unbiased fashion with regard to frequency.

The four basic parameters for the wavelet bank design $k_p$, $N_{dp}$, $w_p$, $N_{ip}$ thus describe the bandpass and stopband behavior of the wavelet bands. In some implementations, the three analytic wavelet bands are chosen to have, for example, nominal (approximate) center frequencies of 24, 16, and 8 Hz. These bands are associated with the scales of QRS features in combination over a wide range of morphologies. Using for example a sample rate of 200 Hz for the ECG and the discrete-time wavelet operators, the bandpass wavelets of the analytic wavelet bank 102 can be implemented using the following design parameters:

TABLE 1

| Band | $k_p$ | $N_{dp}$ | $w_p$ | $N_{ip}$ |
|---|---|---|---|---|
| 1 | 4 | 8 | 3 | 4 |
| 2 | 6 | 6 | 5 | 4 |
| 3 | 12 | 6 | 9 | 4 |

Note that having $k_p$ even for $N_p$ even and having $N_{ip}$ even will make the intrinsic delays of the wavelets an integer number of samples (see U.S. Pat. No. 7,706,992). This in turn allows for the wavelets in the bank to be time-aligned using simple integer-valued alignment delays as described in U.S. Pat. No. 7,706,992. The scales shown are thus chosen as the nearest values to the target that also satisfy the delay-based criteria.

Figure 2:
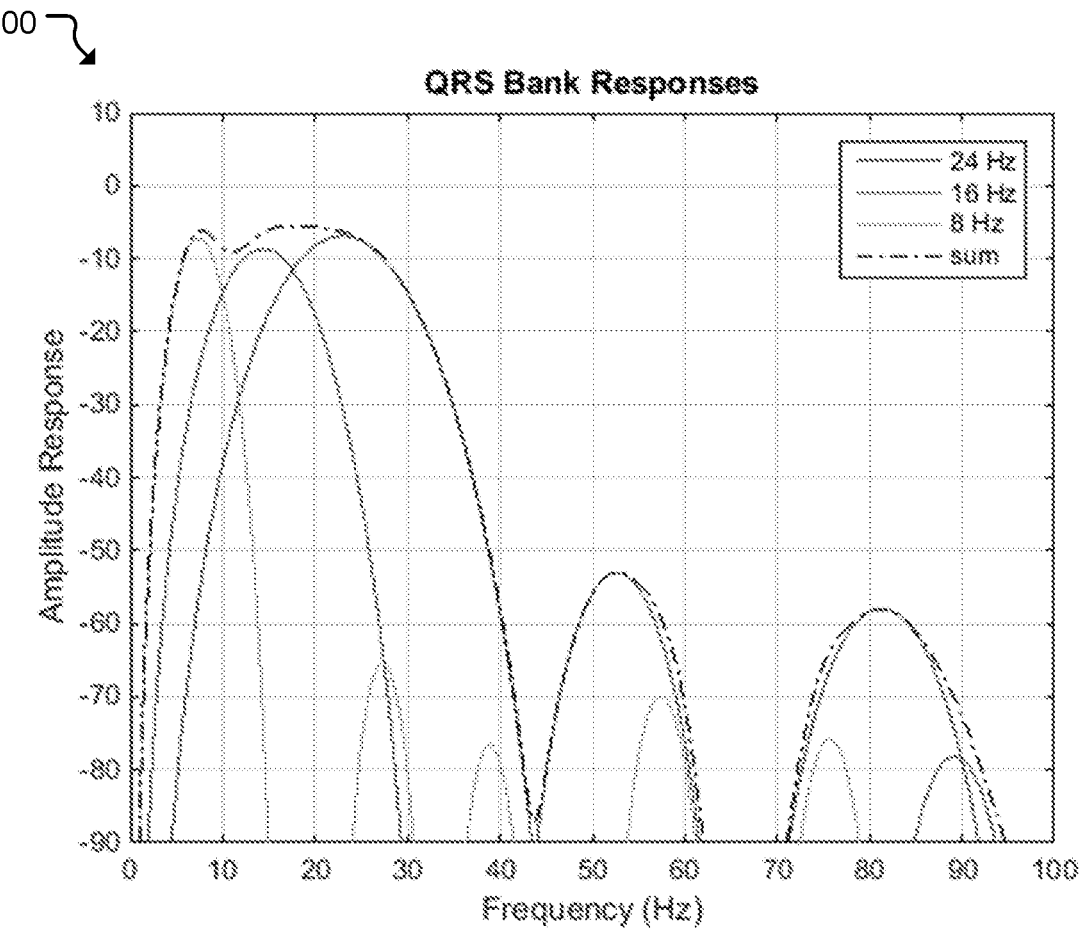
FIG. 2 is a plot showing frequency responses for the real part of the analytic wavelet bank.

The frequency responses resulting from implementing the above parameters are shown in plot 200 of FIG. 2, which shows frequency responses for the real part of the analytic wavelet bank. In plot 200, the dashed line represents the sum of the band responses. The bands are intrinsically linear-phase, and are time-aligned according to their intrinsic delays to form a filter bank as described in U.S. Pat. No. 7,706,992. The bank may also be analytic form, so that each band has two associated outputs, one for the real part of the component and another for the imaginary part of the component. Alternatively, the component output can be considered as a single, complex-valued signal.

Figure 3:
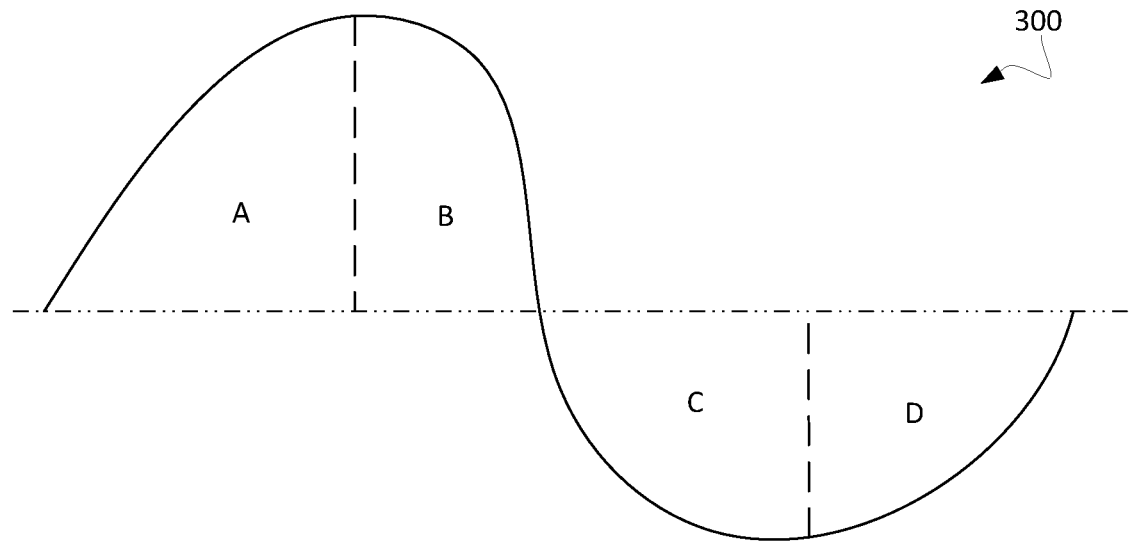
FIG. 3 is a waveform illustrating a cycle from one component signal that is broken up into four quarter-phases.

Referring to FIG. 1, the QP object transform unit 104 detects QP transitions on each of the component signals received from analytic wavelet bank 102. FIG. 3 is a waveform 300 illustrating an example where a cycle from one component signal is broken up into four quarter-phases, labeled as A, B, C, and D. This component signal is broken up into and, in some implementations, defined according to certain unique features such as the positive-going and negative-going zero crossings, and the positive and negative peaks of the component signal. These unique features are shown in a table format below:

TABLE 3

| QP Label | Starts at | Ends at |
|---|---|---|
| A | Positive-going zero crossing | Positive peak |
| B | Positive peak | Negative-going zero crossing |
| C | Negative-going zero crossing | Negative peak |
| D | Negative peak | Positive-going zero crossing |

Referring again to FIG. 1, the QP object transform unit 104 forms, at each QP transition, a QP object (e.g., a data structure) which collects QP attributes (e.g., in data fields) as described in U.S. Pat. No. 7,706,992. For purposes of QRS complex detection, the QP objects contain the time index and component amplitude at the time point of QP detection. QP object streams from the three component bands can be stored in time context for synchronized pattern analysis across the components.

The QP peak detection 106 applies rules for detection of peak patterns associated with QRS complex peaks. For QP peak-pattern detection, amplitude-peak patterns are detected on all QP object streams. In some implementations, two peak patterns are defined along the sequence of QPs as follows:

Peak Pattern A

Over a support of 7 consecutive QPs

The center QP has the largest associated amplitude

Rationale: This pattern corresponds to the sharp central-peak shape

Peak Pattern B

Over a sequence of 3 QPs separated sequentially by 4 consecutive QPs (for a total support of 9 consecutive QPs)

The QP amplitude for the sequence QPs increases monotonically toward the center from both sides Rationale: This pattern corresponds to the general wide-peak shape These specific patterns were determined empirically by matching peak patterns over a large range of observed beat morphologies. The peak patterns are aligned at the center QPs of each pattern. The central QP at which all peak patterns are simultaneously satisfied is marked as a detected QP peak for that QP stream, and collected along with its band and time context including the QP peak time and amplitude and provided to the time qualification unit 108.

QP amplitude peaks generally align in time across their associated bands for actual QRS complexes and not align for artifacts and other features such as those occurring during repolarization. Based upon this time coincidence, the time qualification unit 108 compares pairwise peak times for detected QP peaks for closeness in time to nearest peak times on the other QP bands. QP peaks from at least two bands occurring mutually within a qualification time window are then time-qualified and collected. The qualification time window may be set, for example, at 40 milliseconds, based upon initial observation and optimization of this parameter.

Time-qualified per-band peaks are consolidated into a "central" time-qualified peak with a single computed peak time and amplitude. The consolidated peak time is computed as the mean of the qualified per-band peak times. The consolidated peak amplitude is computed as the total root mean square (RMS) amplitude of the wavelet outputs, evaluated at the consolidated peak time. A stream of time-qualified peaks is thus formed from the series of consolidated peaks and provided to the amplitude qualification unit 110.

The amplitude qualification unit 110 then qualifies the time-qualified peaks for amplitude based upon two criteria:

Relative amplitude criterion

A moving amplitude statistic is formed from the stream of time-qualified peak amplitudes, computed as the mean of the upper quartile values of all peak amplitudes occurring, for example, within the preceding 4 seconds (choosing a time length designed to balance response time to sudden drops in amplitude against rejection of amplitude outliers)

The current peak amplitude is greater than the statistic multiplied by a threshold factor, for example, 0.35 (value chosen to balance rejection of peaks not associated with QRS complexes against proper detection of low-amplitude QRS complexes)

Rationale: Rejection of small peaks that are outliers in context, that are most likely not associated with actual QRS complexes Absolute amplitude criterion The current peak amplitude is greater than a fixed amplitude threshold, for example, 3.6 microvolts (value chosen to reject peaks in low-amplitude range typically associated with baseline noise)

Rationale: Rejection of extremely small peaks regardless of context

Peaks satisfying both criteria are amplitude-qualified and provided to the refractory rule set 112.

The amplitude-qualified peaks are then qualified through the refractory rule set 112. The objective for the refractory is to reject over sensing of relatively large P-waves or T-waves that still satisfy all preceding criteria. The refractory rules are based upon time proximity (time interval between peaks, inter-peak interval) and the relative amplitude of the current peak and the previous peak. An example of a rule set is as follows:

| Definitions | |
| --- | --- |
| diPeak | inter-peak interval |
| aPeakCurr | current-peak amplitude |
| aPeakPrev | previous-peak amplitude |
| fKeepPrev | "keep previous" condition flag |
| fKeepCurr | "keep current" condition flag |
| kThreshRefr | refractory threshold factor |

Rules

If aPeakCurr>=aPeakPrev

Evaluate left-going criteria

If diPeak<left refractory interval

Evaluate left-going amplitude/time criterion

If satisfied, assert fKeepPrev condition, otherwise de-assert

Otherwise, assert fKeepPrev

Perform "keep-previous" actions

If fKeepPrev

Assert new beat detection

Output previous peak as detected beat

Save current peak as previous peak

Otherwise

De-assert new beat detection

Save current peak as previous peak

Otherwise (aPeakPrev>aPeakCurr)

Evaluate right-going criteria

If diPeak<right refractory interval

Evaluate right-going amplitude/time criterion

If satisfied, assert fKeepCurr condition, otherwise de-assert

Otherwise, assert fKeepCurr

Perform "keep-current" actions

If fKeepCurr

Assert new beat detection

Output previous peak as detected beat

Save current peak as previous peak

Otherwise

De-assert new beat detection

Do nothing else (discard current peak)

Left-Going Amplitude/Time Criterion $$(\text{left refractory slope}) = 1/((\text{left refractory interval}) - (\text{left hard refractory interval}))$$

$$k\text{ThreshRefr} = 1 - (di\text{Peak} - (\text{left hard refractory interval})) * (\text{left refractory slope})$$

Satisfied if: $a\text{PeakPrev} >= a\text{PeakCurr} * k\text{ThreshRefr}$

Right-Going Amplitude/Time Criterion $$(\text{right refractory slope})=1/((\text{right refractory interval})-$$
$$(\text{right hard refractory interval}))$$

$$k\text{ThreshRefr}=1-(di\text{Peak}-(\text{right hard refractory interval}))*(\text{right refractory slope})$$

Satisfied if: $a\text{PeakCurr}>=a\text{PeakPrev}*k\text{ThreshRefr}$

Parameters for the left and right going criteria may be determined empirically through optimization as follows:

TABLE 2

| left refractory interval | 350 milliseconds |
|---|---|
| left hard refractory interval | 150 milliseconds |
| right refractory interval | 400 milliseconds |
| right hard refractory interval | 150 milliseconds |

The ECG processing system 100 can be useful in any setting where a patient's heart rate is to be monitored or statistically analyzed, including intensive care, operating, recovery, and emergency and hospital ward settings. The system 100 can provide continuous and immediate heart beat detection and heart rate values, which are of critical importance in emergency medicine and are also very useful for patients with respiratory or cardiac problems, especially chronic obstructive pulmonary disease (COPD), or for diagnosis of heart rhythm disturbances.

Figure 4A:
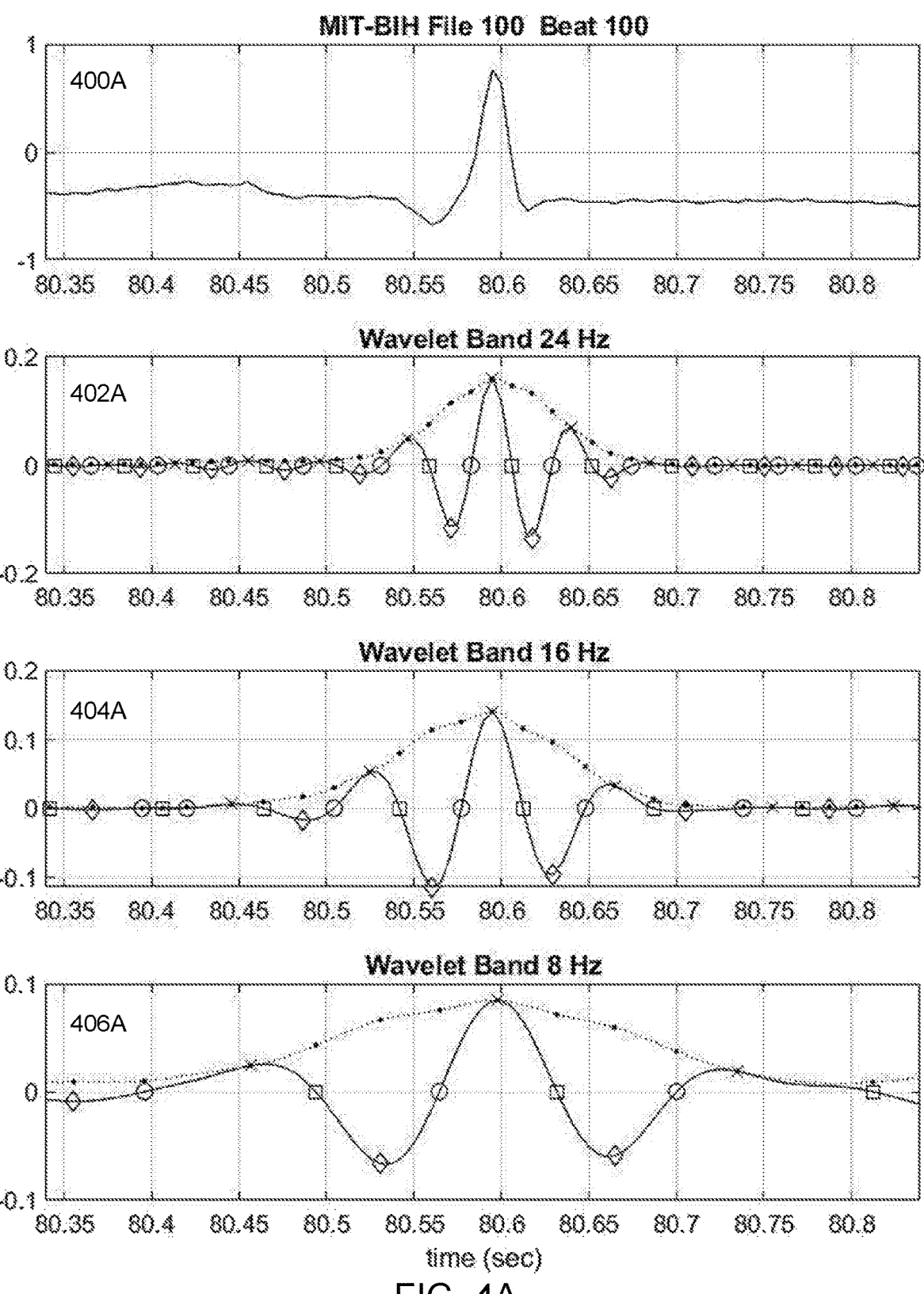
FIGS. 4A and 4B are time traces showing examples of time-aligned wavelet outputs in response to single isolated beats in an ECG.
Figure 4B:
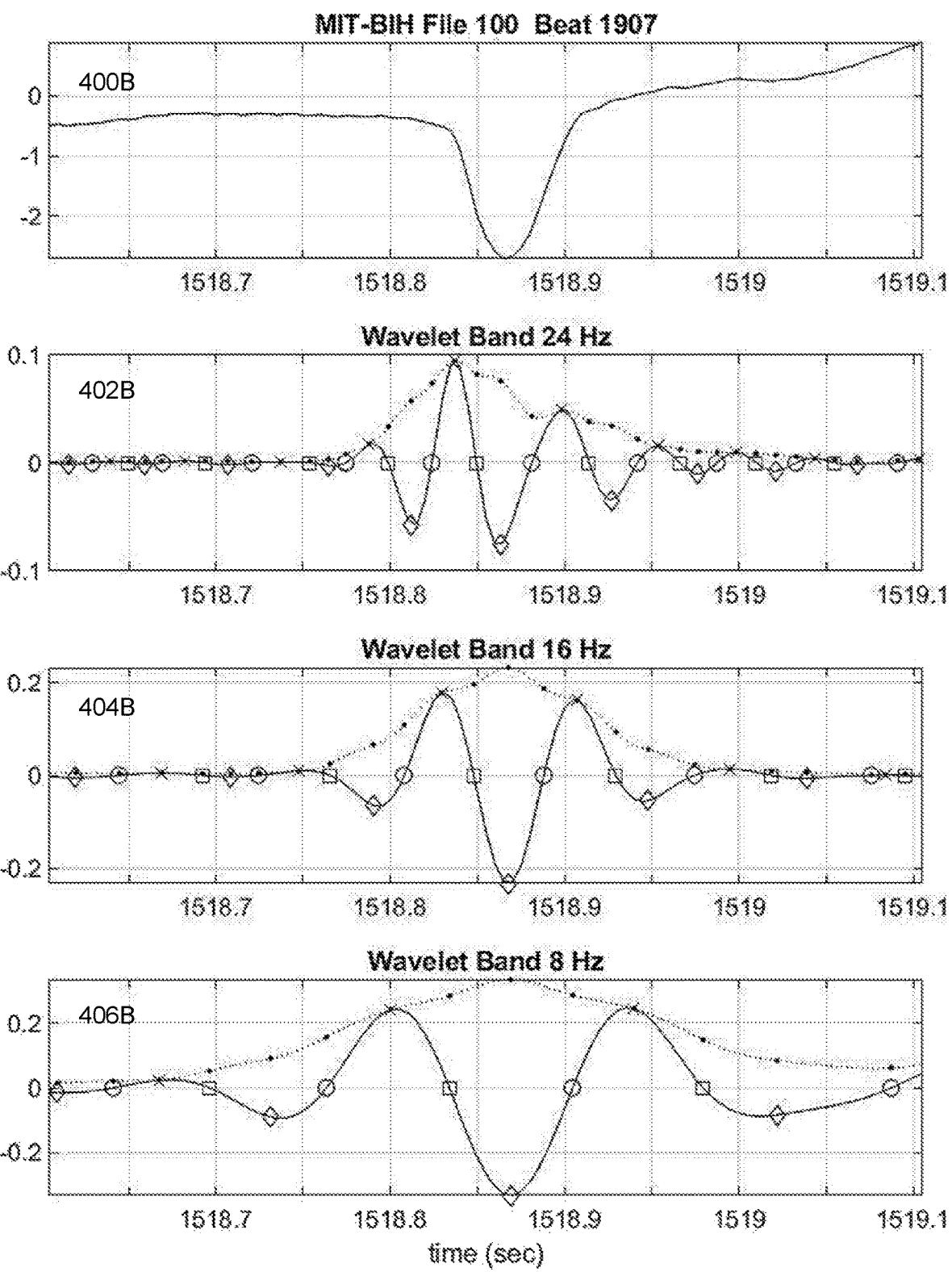

FIGS. 4A and 4B are time traces showing examples of the time-aligned wavelet outputs in response to single isolated beats in an ECG (trace 400A of FIG. 4A and trace 400B of FIG. 4B obtained from File 100 from the MIT-BIH Arrhythmia Database (https://physionet.org/physiobank/database/mitdb/)). All of the time traces show the time period from 250 milliseconds preceding to 250 milliseconds following the beat detection point. The trace 400A of FIG. 4A shows beat 100 in the record, which is a Normal Sinus Rhythm (NSR) beat, while the trace 400B of FIG. 4B shows beat 1907 in the record, which is a Premature Ventricular Contraction (PVC) beat. The traces 402A and 402B show the output of the upper example wavelet band at 24 Hz; the traces 404A and 404B show the output of the middle example wavelet band at 16 Hz; and the traces 406A and 406B show the output of the lower example wavelet band at 8 Hz. For the wavelet output plots, the solid trace is the real part of the analytic wavelet output, while the thinly-dotted trace is the instantaneous amplitude (complex modulus) of the analytic wavelet output. The QP points corresponding to transitions (A, B, C, D) on the wavelet outputs are marked on the real-part waveforms with corresponding symbols (circle, cross, square, diamond), respectively. The corresponding points are also marked on the amplitude outputs with larger dots at the corresponding QP times.

Figure 5:
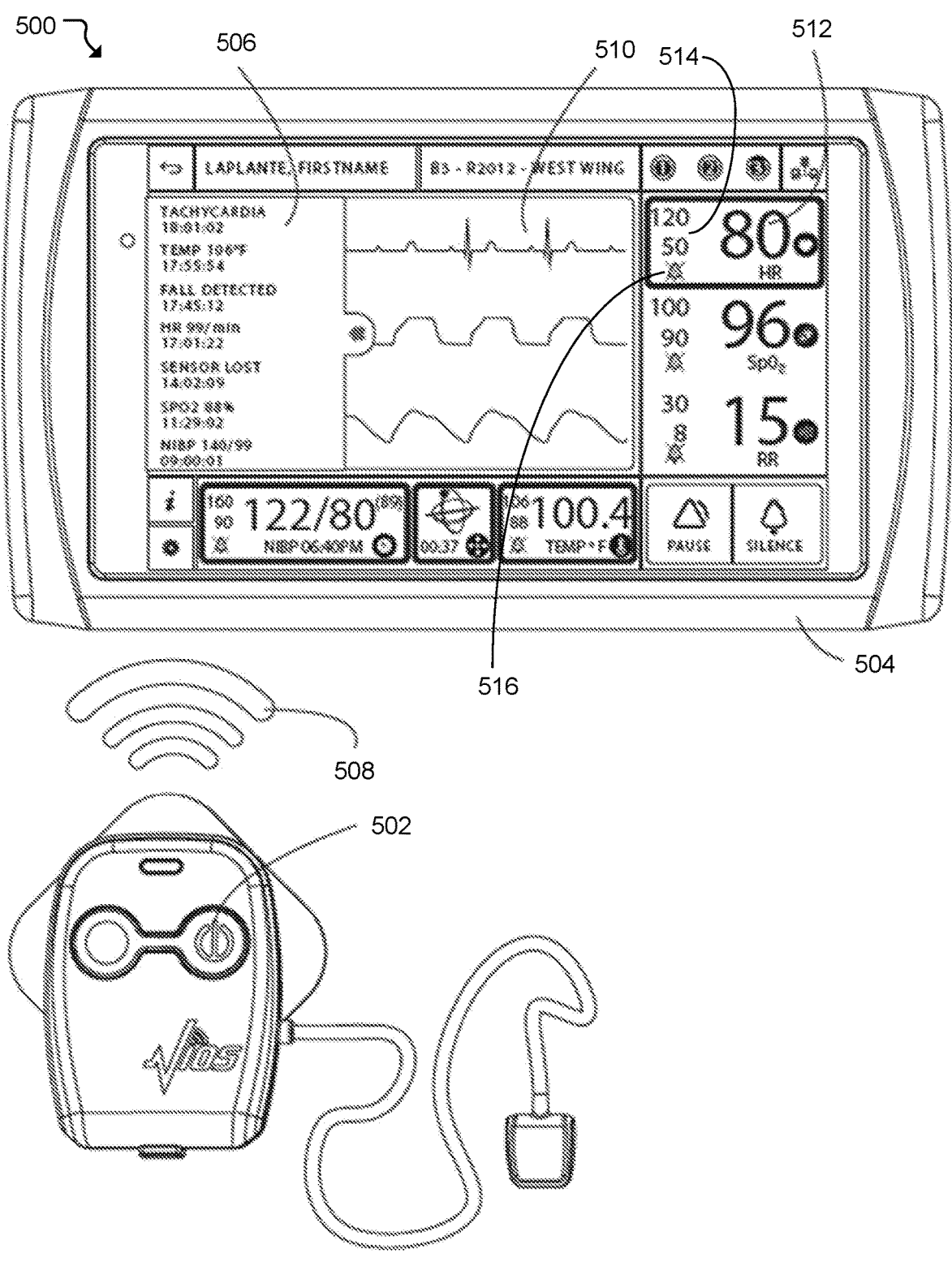
FIG. 5 shows an example of an ECG signal processing system that includes a patient worn sensor in communication with a display device.

FIG. 5 shows a system 500 that includes a patient worn sensor 502 in communication with a display device 504, such as a display of a bedside monitor, a central server station, or a mobile device as described in U.S. Publication No. 2015/0302539. The display device 504 displays information for a patient. The display device 504 can display a user interface 506 that includes information received from the patient worn sensor 502 and/or information associated with a patient associated with the patient worn sensor 502. The patient worn sensor 502 can be, for example, a chest sensor as described in U.S. Publication No. 2015/0302539. The patient worn sensor 502 can include contacts for attaching to the skin of a patient and recording various patient vital signs such as blood pressure, body temperature, respiratory rate, body impedance, blood oxygenation, heart rhythm (via ECG), and heart rate.

The patient worn sensor 502 can wirelessly communicate with the display device 504 through a wireless connection 508 using a wireless communication protocol such as, for example, Bluetooth, Wi-Fi, or a cellular protocol. The patient worn sensor 502 can transmit vital sign information for the patient to the display device 504 through the wireless connection 508. In some implementations, the patient worn sensor 502 can perform processing on the collected vital sign information, such as the ECG signal processing described above, prior to transmission of the information to the display device 504, while in some implementations, the patient worn sensor 502 can transmit raw vital sign information to the display device 504 instead of or in addition to processed information.

The display device 504 can be a touch screen device, such as a tablet, that is capable of receiving touch screen inputs. In some implementations, the display device 504 can receive input from a keyboard, mouse, input buttons, or one or more devices capable of recognizing voice commands. In some implementations, the display device 504 can be controlled using a device in wireless communication with the display device 504, such as a mobile phone. In some implementations, the display device 504 is a "headless" device that does not include direct user input and/or output functionality, but rather merely serves as a processing device for processing raw vital sign information received from the patient worn sensor 502, detecting alarm states, transmitting alerts to other devices in communication with the display device 504, and transmitting patient information to one or more central servers. In such cases, the display device 504 would not include a display.

The user interface 506 displays information for a patient associated with the patient worn sensor 502. For example, electrodes of the patient worn sensor 502 can be in contact with the patient's skin and collect vital sign information which is transferred to the display device 504 through the wireless connection 508, processed by the display device 504, and displayed as part of the user interface 506. The user interface 506 shows various vital sign waves and numeric levels.

For example, the user interface 506 shows an ECG waveform 510 for the patient as well as a numeric heart rate value 512 for the patient. In the example shown, the heart rate value 512 for the patient is 80 beats per minute. The per-beat heart rate in beats per minute (BPM) can be computed as HR=60/RR where RR is the R-R interval in seconds. The R-R interval can be found for the current beat as the time difference between the current beat detection time and the preceding beat detection time. In addition, the consolidated peak time can be marked on the ECG display at the appropriate point on the time axis.

The user interface 506 indicates an acceptable heart rate range 514 for the patient as falling between 50 and 120 beats per minute. Being as the current heart rate 512 for the patient of 80 beats per minute falls within the indicated acceptable range 514, there is not currently an alarm state for heart rate for the patient. This is indicated by an icon 516 of a bell superimposed with an "X" symbol. The icon 516 indicates that the current heart rate of the patient is within the acceptable range. In a situation in which the heart rate for the patient is not within the acceptable level, the icon 516 can change to indicate an alarm state. For example, the "X" can disappear from the icon 516 and the icon 516 can light up or flash to indicate an alarm state. Additionally, the display device 504 can emit an audible alarm to alert nearby caregivers to an alarm state for the patient. In some implementations, other portions of the user interface 506 can flash or otherwise indicate an alarm state. For example, the displayed heart rate value 512 can flash when the patient's heart rate is outside of the acceptable range 514. In some implementations, the icon 516 (or other portions of the user interface 506) can flash at varying rates to indicate the severity of a particular alarm state. For example, the icon 516 can flash faster the further the patient's heart rate is from the acceptable range.

Figure 6:
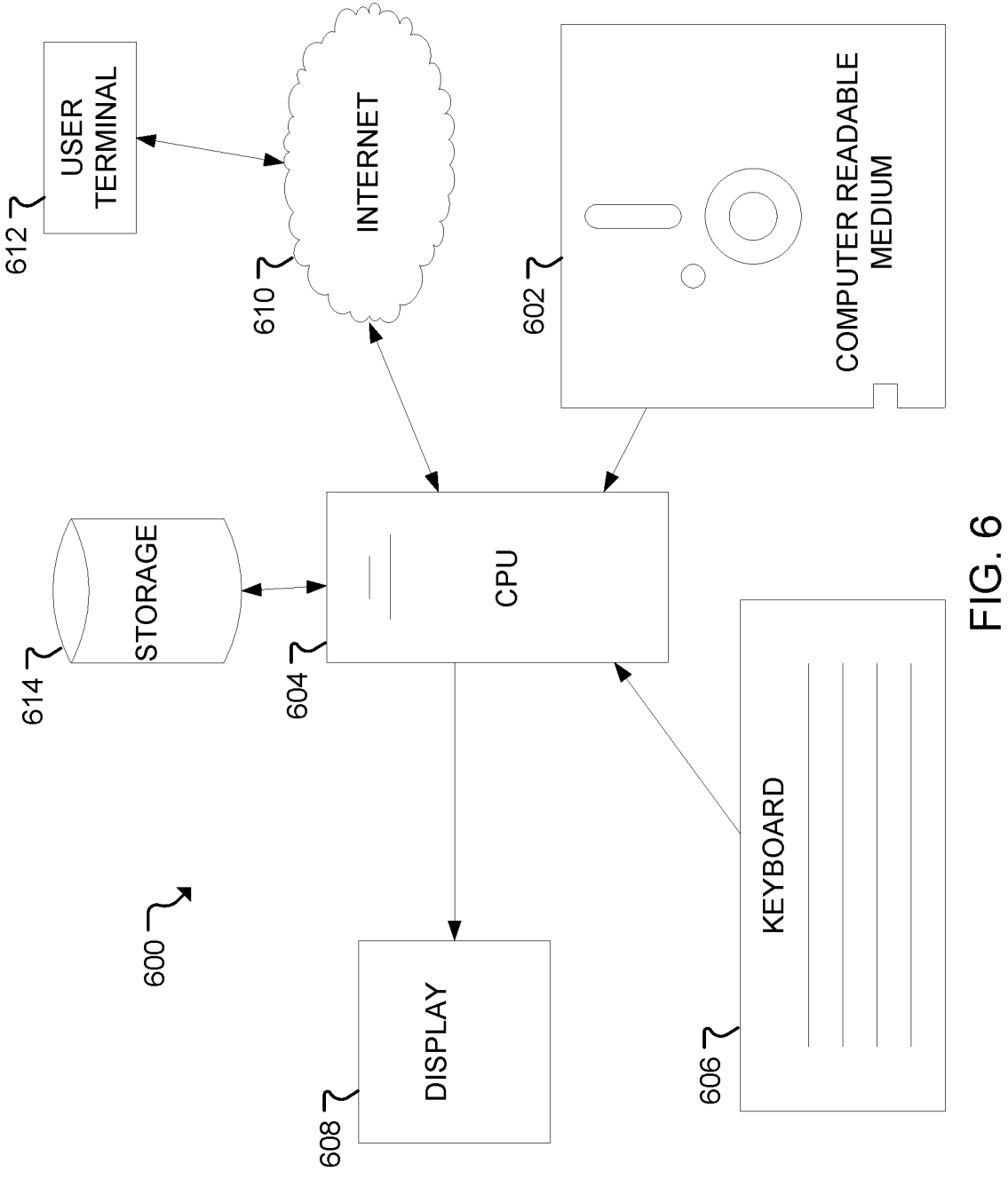
FIG. 6 is a block diagram showing an example of a computing system that may be used to implement an ECG signal processing system.

FIG. 6 is a block diagram showing an example of a computing system 600 executing a computer program that implements the above-described operations, data structures, and/or programs contained on a computer readable medium 602, and executed by a central processing unit (CPU) 604. The CPU 604 may be an x86 series CPU or other CPU known in the art. Input to execute the program can, in some implementations, come by way of a keyboard 606. In some implementations, input to execute the program can come by way of a peripheral device such as a mouse, light pen, touch screen, touch pad, or any other input device known in the art. In some implementations, the described operations can be called by another program to execute and process oximetry data. Once processed, data processed using the above-described operations, data structures, and/or programs can be outputted to a display 608, or sent via an internet 610 or other wireless communications channel to another user terminal 612. In some implementations, the output can be placed into a database 614 or another database located off-site.

Figure 7:
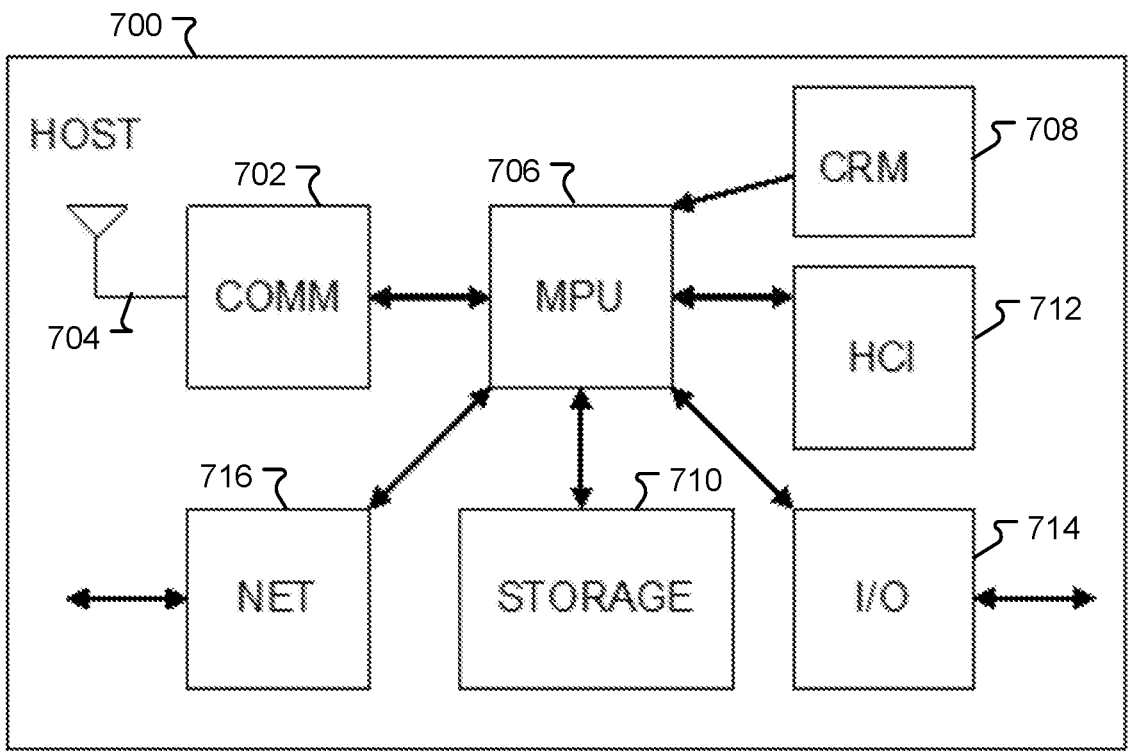
FIG. 7 is a block diagram showing an example of a computing system that depicts a host system that may be used to implement an ECG signal processing system.

FIG. 7 is a block diagram showing an example of a computing system that depicts a host 700 which may, in some implementations, include a set of units or modules such as a communications module (COMM) 702 and associated communications link 704 for communicating with a patient worn sensor, a microprocessor unit (MPU) 706 including a computer readable medium (CRM) 708 containing a set of application instructions, an associated storage module 710 for storing patient data, a human-computer interface (HCI) 712 by which an operator (e.g., a physician, technician, or patient) may interact with the MPU 706 and which may include a visual display, auditory display, keyboard, mouse, touch screen, haptic device, or other means of interaction. The host 700 also includes an input/output (I/O) module 714 for generally connecting to, and communicating with, computer peripherals such as for example printers, scanners, and/or data acquisition or imaging equipment, and a network communications module (NET) 716 for communicating with other hosts on a computer network such as Ethernet and/or a wireless network, or Wi-Fi.

FIG. 8 is a flowchart showing examples of operations 800 performed by an ECG signal processing system that detects QRS complexes. The operations 800 may be performed by a system of one or more computers, such as the system of FIG. 1. The operations 800 may include details that have been discussed above.

At 802, a signal corresponding to electrical activity of a patient's heart, e.g., an ECG signal, is received.

At 804, the signal is separated into component signals, where each of the component signals represents a frequency-limited band. Separating the signal into the component signals may include filtering the signal using a bank of three bandpass filters.

At 806, fractional phase transitions for each of the component signals are detected. Detecting the fractional phase transitions for each of the component signals may include detecting positive-going crossings, negative-going zero crossings, positive peaks, and negative peaks of the component signal.

At 808, a data object containing a time value and an amplitude value is generated at each of the detected fractional phase transitions for each of the component signals.

At 810, a peak amplitude is detected for a set of consecutive data objects associated with a first component signal of the component signals based on the amplitude value of each data object of the set of consecutive data objects and a peak amplitude is detected for a set of consecutive data objects associated with a second component signal of the component signals based on the amplitude value of each data object of the set of consecutive data objects. In some implementations, detecting the peak amplitude includes detecting the peak amplitude at a center data object of the set of consecutive data objects. In some implementations, detecting the peak amplitude includes detecting amplitude values that monotonically increase toward and monotonically decrease away from the peak amplitude at a center data object of the set of consecutive data objects.

At 812, a determination is made that the peak amplitudes satisfy a first time criterion based on the time values of the data objects corresponding to the peak amplitudes. Determining that the peak amplitudes satisfy the first time criterion may include determining that the time values occur within a time window.

At 814, a consolidated peak amplitude and a consolidated peak time is calculated based on the peak amplitudes and the time values of the data objects corresponding to the peak amplitudes. In some implementations, calculating the consolidated peak amplitude includes calculating a total root mean square amplitude of the amplitude values of the component signals at the consolidated peak time. In some implementations, calculating the consolidated peak time includes calculating a mean of the time values.

At 816, a determination is made that the consolidated peak amplitude satisfies both an amplitude criterion and a second time criterion. In some implementations, determining that the consolidated peak amplitude satisfies the amplitude criterion includes calculating a moving amplitude statistic from a stream of consolidated peak amplitudes and determining that the consolidated peak amplitude is greater than the moving amplitude statistic multiplied by a threshold factor. In some implementations, determining that the consolidated peak amplitude satisfies the amplitude criterion includes determining that the consolidated peak amplitude is greater than a fixed amplitude threshold. In some implementations, determining that the consolidated peak amplitude satisfies the amplitude criterion includes determining a relative amplitude of the consolidated peak amplitude and a previous consolidated peak amplitude. In some implementations, determining that the consolidated peak amplitude satisfies the second time criteria includes determining a time interval between the consolidated peak amplitude and a previous consolidated peak amplitude.

At 818, an indication of a detected heartbeat is provided in response to determining that the consolidated peak amplitude satisfies both the amplitude criterion and the second time criterion.

The features described in this disclosure can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor, and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing context.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer area processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application specific integrated circuits). To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet. The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as Such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software or hardware product or packaged into multiple software or hardware products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A non-transitory computer readable storage medium encoded with a computer program, the program comprising instructions that when executed by one or more data processing apparatus cause the one or more data processing apparatus to perform operations comprising:

receiving an electrocardiogramal corresponding to electrical activity of a patient's heart;

separating the electrocardiogramaignal into component signals, wherein each of the component signals represents a frequency-limited band;

detecting fractional phase transitions for each of the component signals;

generating, at each of the detected fractional phase transitions for each of the component signals, a data object containing a time value and an amplitude value;

for a set of consecutive data objects associated with a first component signal of the component signals, detecting a peak amplitude based on the amplitude value of each data object of the set of consecutive data objects in real time;

for a set of consecutive data objects associated with a second component signal of the component signals, detecting a peak amplitude based on the amplitude value of each data object of the set of consecutive data objects in real time;

determining that the peak amplitudes satisfy a first time criterion based on the time values of the data objects corresponding to the peak amplitudes in real time;

calculating a consolidated peak amplitude and a consolidated peak time based on the peak amplitudes and the time values of the data objects corresponding to the peak amplitudes in real time;

determining that the consolidated peak amplitude satisfies both an amplitude criterion and a second time criterion in real time; and in response to determining that the consolidated peak amplitude satisfies both the amplitude criterion and the second time criterion, continuously providing an indication of a detected heartbeat in real time.

2. The non-transitory computer readable storage medium of claim 1, wherein separating the electrocardiogramaignal into the component signals comprises filtering the electrocardiogramaignal using a bank of three bandpass filters.

3. The non-transitory computer readable storage medium of claim 1, wherein detecting the fractional phase transitions for each of the component signals comprises detecting positive-going crossings, negative-going zero crossings, positive peaks, and negative peaks of the component signal.

4. The non-transitory computer readable storage medium of claim 1, wherein detecting the peak amplitude based on the amplitude value of each data object of the set of consecutive data objects comprises detecting the peak amplitude at a center data object of the set of consecutive data objects.

5. The non-transitory computer readable storage medium of claim 1, wherein detecting the peak amplitude based on the amplitude value of each data object of the set of consecutive data objects comprises detecting amplitude values that monotonically increase toward and monotonically decrease away from the peak amplitude at a center data object of the set of consecutive data objects.

6. The non-transitory computer readable storage medium of claim 1, wherein determining that the peak amplitudes satisfy the first time criterion based on the time values of the data objects corresponding to the peak amplitudes comprises determining that the time values occur within a time window.

7. The non-transitory computer readable storage medium of claim 1, wherein calculating the consolidated peak amplitude comprises calculating a total root mean square amplitude of the amplitude values of the component signals at the consolidated peak time.

8. The non-transitory computer readable storage medium of claim 1, wherein calculating the consolidated peak time comprises calculating a mean of the time values.

9. The non-transitory computer readable storage medium of claim 1, wherein determining that the consolidated peak amplitude satisfies the amplitude criterion comprises:

calculating a moving amplitude statistic from a stream of consolidated peak amplitudes; and determining that the consolidated peak amplitude is greater than the moving amplitude statistic multiplied by a threshold factor.

10. The non-transitory computer readable storage medium of claim 1, wherein determining that the consolidated peak amplitude satisfies the amplitude criterion comprises determining that the consolidated peak amplitude is greater than a fixed amplitude threshold.

11. The non-transitory computer readable storage medium of claim 1, wherein determining that the consolidated peak amplitude satisfies the amplitude criterion comprises determining a relative amplitude of the consolidated peak amplitude and a previous consolidated peak amplitude.

12. The non-transitory computer readable storage medium of claim 1, wherein determining that the consolidated peak amplitude satisfies the second time criteria comprises determining a time interval between the consolidated peak amplitude and a previous consolidated peak amplitude.

13. A computer-implemented method comprising:

receiving an electrocardiogramal corresponding to electrical activity of a patient's heart;

separating the electrocardiogramaignal into component signals, wherein each of the component signals represents a frequency-limited band;

detecting fractional phase transitions for each of the component signals;

generating, at each of the detected fractional phase transitions for each of the component signals, a data object containing a time value and an amplitude value;

for a set of consecutive data objects associated with a first component signal of the component signals, detecting a peak amplitude based on the amplitude value of each data object of the set of consecutive data objects in real time;

for a set of consecutive data objects associated with a second component signal of the component signals, detecting a peak amplitude based on the amplitude value of each data object of the set of consecutive data objects in real time;

determining that the peak amplitudes satisfy a first time criterion based on the time values of the data objects corresponding to the peak amplitudes in real time;

calculating a consolidated peak amplitude and a consolidated peak time based on the peak amplitudes and the time values of the data objects corresponding to the peak amplitudes in real time;

determining that the consolidated peak amplitude satisfies both an amplitude criterion and a second time criterion in real time; and in response to determining that the consolidated peak amplitude satisfies both the amplitude criterion and the second time criterion, continuously providing an indication of a detected heartbeat in real time.

14. The computer-implemented method of claim 13, wherein separating the electrocardiogramaignal into the component signals comprises filtering the electrocardiogramal using a bank of three bandpass filters.

15. The computer-implemented method of claim 13, wherein detecting the fractional phase transitions for each of the component signals comprises detecting positive-going crossings, negative-going zero crossings, positive peaks, and negative peaks of the component signal.

16. The computer-implemented method of claim 13, wherein detecting the peak amplitude based on the amplitude value of each data object of the set of consecutive data objects comprises detecting the peak amplitude at a center data object of the set of consecutive data objects.

17. The computer-implemented method of claim 13, wherein detecting the peak amplitude based on the amplitude value of each data object of the set of consecutive data objects comprises detecting amplitude values that monotonically increase toward and monotonically decrease away from the peak amplitude at a center data object of the set of consecutive data objects.

18. The computer-implemented method of claim 13, wherein determining that the peak amplitudes satisfy the first time criterion based on the time values of the data objects corresponding to the peak amplitudes comprises determining that the time values occur within a time window.

19. The computer-implemented method of claim 13, wherein calculating the consolidated peak amplitude comprises calculating a total root mean square amplitude of the amplitude values of the component signals at the consolidated peak time.

20. The computer-implemented method of claim 13, wherein calculating the consolidated peak time comprises calculating a mean of the time values.

21. The computer-implemented method of claim 13, wherein determining that the consolidated peak amplitude satisfies the amplitude criterion comprises:

calculating a moving amplitude statistic from a stream of consolidated peak amplitudes; and determining that the consolidated peak amplitude is greater than the moving amplitude statistic multiplied by a threshold factor.

22. The computer-implemented method of claim 13, wherein determining that the consolidated peak amplitude satisfies the amplitude criterion comprises determining that the consolidated peak amplitude is greater than a fixed amplitude threshold.

23. The computer-implemented method of claim 13, wherein determining that the consolidated peak amplitude satisfies the amplitude criterion comprises determining a relative amplitude of the consolidated peak amplitude and a previous consolidated peak amplitude.

24. The computer-implemented method of claim 13, wherein determining that the consolidated peak amplitude satisfies the second time criteria comprises determining a time interval between the consolidated peak amplitude and a previous consolidated peak amplitude.

25. A system comprising:

a sensor configured to detect electrical activity of a patient's heart;

a display apparatus;

one or more data processing apparatus coupled with the sensor and the display apparatus; and a non-transitory computer readable storage medium encoded with a computer program, the program comprising instructions that when executed by the one or more data processing apparatus cause the one or more data processing apparatus to perform operations comprising:

receiving an electrocardiogramal corresponding to electrical activity of a patient's heart;

separating the electrocardiogramaignal into component signals, wherein each of the component signals represents a frequency-limited band;

detecting fractional phase transitions for each of the component signals;

generating, at each of the detected fractional phase transitions for each of the component signals, a data object containing a time value and an amplitude value;

for a set of consecutive data objects associated with a first component signal of the component signals, detecting a peak amplitude based on the amplitude value of each data object of the set of consecutive data objects in real time;

for a set of consecutive data objects associated with a second component signal of the component signals, detecting a peak amplitude based on the amplitude value of each data object of the set of consecutive data objects in real time;

determining that the peak amplitudes satisfy a first time criterion based on the time values of the data objects corresponding to the peak amplitudes in real time;

calculating a consolidated peak amplitude and a consolidated peak time based on the peak amplitudes and the time values of the data objects corresponding to the peak amplitudes in real time;

determining that the consolidated peak amplitude satisfies both an amplitude criterion and a second time criterion in real time; and in response to determining that the consolidated peak amplitude satisfies both the amplitude criterion and the second time criterion, continuously providing an indication of a detected heartbeat in real time.

26. The system of claim 25, wherein separating the electrocardiogramal into the component signals comprises filtering the electrocardiogramal using a bank of three band-pass filters.

27. The system of claim 25, wherein detecting the fractional phase transitions for each of the component signals comprises detecting positive-going crossings, negative-going zero crossings, positive peaks, and negative peaks of the component signal.

28. The system of claim 25, wherein detecting the peak amplitude based on the amplitude value of each data object of the set of consecutive data objects comprises detecting the peak amplitude at a center data object of the set of consecutive data objects.

29. The system of claim 25, wherein detecting the peak amplitude based on the amplitude value of each data object of the set of consecutive data objects comprises detecting amplitude values that monotonically increase toward and monotonically decrease away from the peak amplitude at a center data object of the set of consecutive data objects.

30. The system of claim 25, wherein determining that the peak amplitudes satisfy the first time criterion based on the time values of the data objects corresponding to the peak amplitudes comprises determining that the time values occur within a time window.

31. The system of claim 25, wherein calculating the consolidated peak amplitude comprises calculating a total root mean square amplitude of the amplitude values of the component signals at the consolidated peak time.

32. The system of claim 25, wherein calculating the consolidated peak time comprises calculating a mean of the time values.

33. The system of claim 25, wherein determining that the consolidated peak amplitude satisfies the amplitude criterion comprises:

calculating a moving amplitude statistic from a stream of consolidated peak amplitudes; and determining that the consolidated peak amplitude is greater than the moving amplitude statistic multiplied by a threshold factor.

34. The system of claim 25, wherein determining that the consolidated peak amplitude satisfies the amplitude criterion comprises determining that the consolidated peak amplitude is greater than a fixed amplitude threshold.

35. The system of claim 25, wherein determining that the consolidated peak amplitude satisfies the amplitude criterion comprises determining a relative amplitude of the consolidated peak amplitude and a previous consolidated peak amplitude.

36. The system of claim 25, wherein determining that the consolidated peak amplitude satisfies the second time criteria comprises determining a time interval between the consolidated peak amplitude and a previous consolidated peak amplitude.

37. A non-transitory computer readable storage medium encoded with a computer program, the program comprising instructions that when executed by one or more data processing apparatus cause the one or more data processing apparatus to perform operations comprising:

receiving an electrocardiogramaignal corresponding to electrical activity of a patient's heart;

separating the electrocardiogramaignal into component signals, wherein each of the component signals represents a frequency-limited band;

detecting fractional phase transitions for each of the component signals;

generating, at each of the detected fractional phase transitions for each of the component signals, a data object containing a time value and an amplitude value;

for a set of consecutive data objects, detecting a peak amplitude based on the amplitude value of each data object of the set of consecutive data objects in real time;

determining, in real time, that the peak amplitude satisfies both (i) a time criterion based on the time value of the data object corresponding to the peak amplitude and (ii) an amplitude criterion; and in response to determining that the peak amplitude satisfies both the time criterion and the amplitude criterion, continuously providing an indication of a detected heartbeat in real time.

* * * * *